United States Patent [19]

Sawan et al.

[11] Patent Number: 5,224,493
[45] Date of Patent: Jul. 6, 1993

[54] CONTRACEPTIVE INTRACERVICAL DEVICE AND NOVEL NONSYSTEMIC AGENTS FOR THE PREVENTION OF CONCEPTION AND DISEASE

[75] Inventors: Samuel P. Sawan, Tyngsboro; Harli M. Dollinger, Dracut; Herbert W. Horne, Jr., Framingham, all of Mass.

[73] Assignee: Cadco Corporation, Framingham, Mass.

[21] Appl. No.: 648,158

[22] Filed: Jan. 30, 1991

[51] Int. Cl.$^5$ .............................................. A61F 6/14
[52] U.S. Cl. ....................................... 128/832; 128/830
[58] Field of Search ............... 128/830, 832, 833, 837, 128/917

[56] References Cited

U.S. PATENT DOCUMENTS

| | | | |
|---|---|---|---|
| 3,545,439 | 12/1970 | Duncan | 128/832 |
| 3,563,235 | 2/1971 | Zipper | 128/833 |
| 3,803,308 | 4/1974 | Zipper | 128/833 X |
| 3,834,378 | 9/1974 | Lerner et al. | 128/833 |
| 3,920,805 | 11/1975 | Roseman | 128/832 X |
| 4,449,980 | 5/1984 | Millar et al. | 128/830 X |
| 4,807,610 | 2/1989 | Gainutdinova et al. | 128/832 X |
| 5,019,096 | 5/1991 | Fox, Jr. et al. | 623/1 |

Primary Examiner—Robert A. Hafer
Assistant Examiner—Sam Rimell
Attorney, Agent, or Firm—Samuels, Gauthier & Stevens

[57] ABSTRACT

An intracervical device for the controlled release of an active agent for the prevention of both specific sexually transmitted diseases and pregnancy. The device consists of an entirely erodible polymer, or a combination of an erodible polymer with a skeletal polymer capable of maintaining therefor mechanical properties over long duration in the body. The active agents can include one or more than one of a large family of insoluble metal salts which have been shown to affect sperm motility and/or viability and are effacious in the prevention of sexually transmitted diseases. These agents are slowly released over a defined period of time ranging from one month to up to 18 months in duration due to erosion of the polymer matrix.

17 Claims, 4 Drawing Sheets

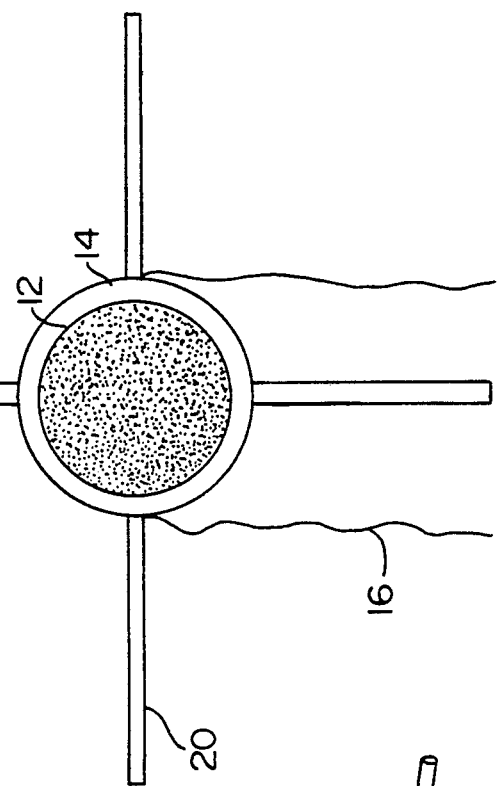
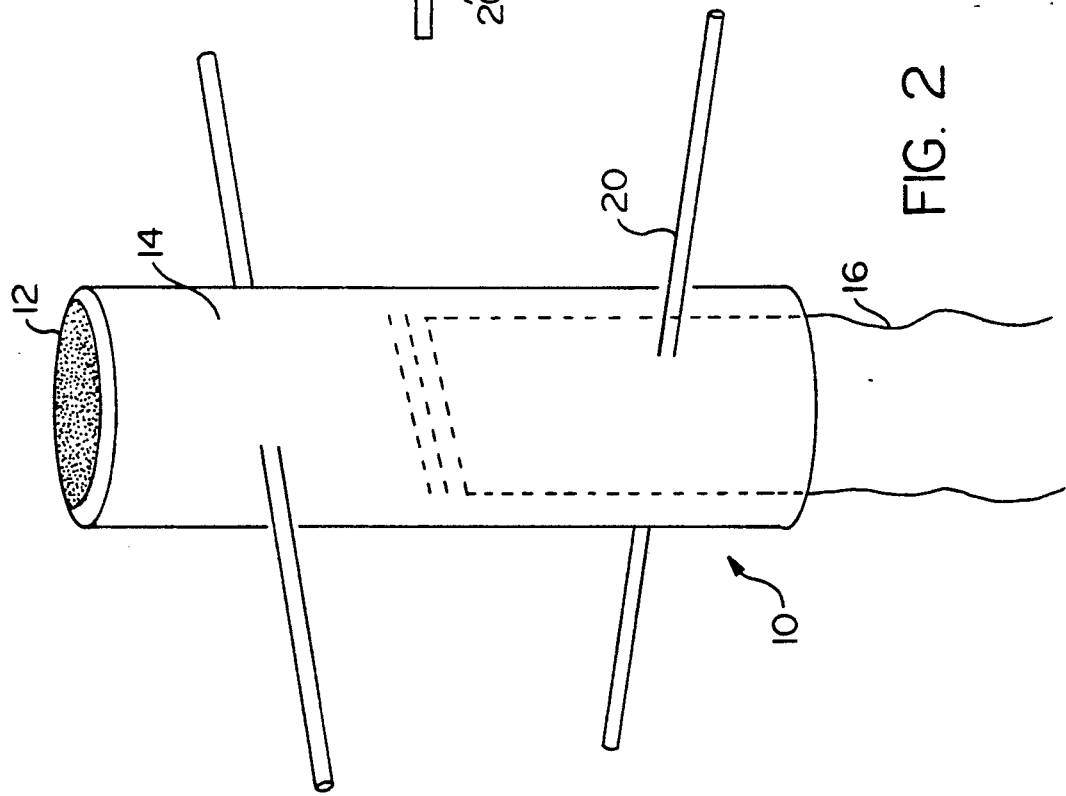

CONTRACEPTIVE INTRACERVICAL DEVICE AND NOVEL NONSYSTEMIC AGENTS FOR THE PREVENTION OF CONCEPTION AND DISEASE

BACKGROUND AND BRIEF SUMMARY OF THE INVENTION

Vaginal contraceptive devices which prevent upward migration of sperm into the cervix are placed in the vaginal canal to block the external os of the cervix. An example of this is a diaphragm which was invented prior to 1882 by the German physician W. P. J. Mensinga and is still in use with only minor modification (Contraceptive Technology; Current and Prospective Methods. S. J. Segal and C. Tietze, Reports on Population/Family Planning, October, 1969). The intent is two-fold: not only to seal off the cervix but more importantly to be a vehicle to ensure that spermicide (foam, cream, jelly, etc.) is placed between the cervix and the site of sperm deposition. With the increased availability of oral and parenteral steroidal contraceptives and of intrauterine (intrafundal) devices (IUD's), the diaphragm is now less commonly the first choice of contraceptives among women.

Devices for the controlled and continuous delivery of an active agent from a polymer excipient for the dual and simultaneous purposes of prevention of disease and of contraception by prohibiting the migration of sperm through the cervical canal are known; see U.S. Pat. No. 4,246,896 and the background discussion therein.

The use of metals and metal compounds for use as contraceptive and/or spermicidal agents can be found in the literature as far back as 1850. Many of the studies involved the use of metals as intrauterine contraceptives. J. Zipper et al (Zipper, J., Medel, M., Prager, R., "Suppression of Fertility by Intrauterine Copper and Zinc in Rabbits", Am. J. Obstet. Gynecol., therefore 105 therefor 529 1969) studied the effects of both copper and zinc in the fundus of the uterus in rabbits. Both metals rendered the rabbits infertile. Subsequent tests by Zipper (Zipper, J., Tatum H., Pastene, L., Medel, M., and Revera, M., "Metallic Copper as an Intrauterine Contraceptive Adjunct to the "T" Device", Am. J. Obstet. Gynecol., therefore 105 therefor 529 1969) showed that copper is also effective in human females. Chang published studies on not only the effects of copper, but also other metals as intrauterine contraceptives (Chang, C., Tatum, H., "A Study of the Antifertility Effect of Intrauterine Copper", Contraception, 1, 256, 1970 and Chang, C., Tatum, H., and Kincl, F., "The Effects of Intrauterine Copper and Other Metals on Implantation in Rats and Hampsters", Fert. and Steril., 21, 274, 1970). These tests proved the efficacy of not only copper, but also cadmium, cobalt, lead, nickel and zinc.

Numerous studies have also been done on the effect of metals and metal compounds and halides as spermicides and antimotility agents. Holland and White ("Heavy Metals and Spermatozoa; Inhibition of the Motility and Metabolism of Spermatozoa by Metals Related to Copper", Fert. and Steril., 35, 5, 1980) examined nickel, zinc, palladium, silver, platinum, cadmium, gold and brass. This study showed that different metals affected different aspects of sperm metabolism such as glycolysis and oxygen utilization. None of these metals showed immediate spermicidal action or immobilization (total testing time was 3 hours). The immobilization activity was as follows:

copper > cadmium > brass > silver > zinc

This study further claimed that immotile therefore spermatozoa even if metabolically active, are incapable of fertilization. Another study which shows similar results is that by Kesseru and Leon ("The Effect of Different Solid Metals and Metallic Pairs on Human Sperm Motility", Int. J. Fert., 19, 81, 1974).

Only two studies were uncovered in the literature on the effects of inorganic salts as spermicidal agents. One study done by J. Narayan and J. Singh ("Spermicidal Activity of Some Halides", Indian J. of Physio. Pharm., 23, 4, 1979) examined the following soluble inorganic salts: cadmium chloride, lithium bromide, ferric chlroide, sodium iodide, mercuric chloride, potassium iodide, sodium bromide, lithium iodide and potassium bromide. All of these compounds were shown to be spermicidal.

In another study, the efficacy of iron salts as spermicidal agents was evaluated (Safya, S., Sikka, S., Sharma, B., and Laumas, K., "A Comparative Evaluation of Spermicidal Activities of Iron Salts", Indian J. of Exp. Biol., 17, 1979). It was shown that direct interaction of sperm with soluble iron salts causes a rapid and irreversible immobilization even at low concentrations. Ferric salts are more potent sperm immobilizing agents than ferrous salts e.g. ferrous ammonium sulfate > ferric chloride.

Testing techniques for spermicidal agents have varied greatly over the years. N. Millman ("A Critical review of Methods Measuring Spermicidal Action", New York Academy of Sciences, 54, 806, 1952) reviewed the breadth of testing techniques and duration. Most of the techniques discussed involved the testing of soluble agents as vaginal contraceptives or hormone regulating agents. Since that time there have been many other reviews, especially originating from Ortho Pharmaceuticals. These reviews discuss spermicidal testing in vitro, in animals and in the human female.

Based on this survey of the prior art, the efficacious use of insoluble compounds, either organic or inorganic for either vaginal or cervical contraception has not been shown.

Broadly our invention comprises a spermicidal composition embodying a novel spermicidal agent and the use of the composition as a spermicide. The agent is selected from the group consisting of insoluble metals, salts and/or oxides of these metals which are not toxic. Insoluble as used herein means insoluble in body fluids when the agent is used for its intended purpose. The metals can be selected from the group consisting of silver, magnesium, zinc, copper, cadmium or arsenic. The metals may be combined with members selected from the group consisting of carbonates, phosphates, halides, lactates, oxides or peroxides. Further, these agents are ideally active against pathogens responsible for sexually transmitted diseases. That is, these agents have also shown efficacy as anti-infectants and antiseptics. Preliminary tests in agar have shown zones of inhibition with urea plasmids which are responsible for many sexually transmitted diseases.

The invention, in a preferred embodiment, embodies the use of insoluble inorganic metallic salts for the prevention of pregnancy. These agents are capable of affecting sperm motility and viability as well as being microstatic or microcidal versus microorganisms responsible for various sexually transmitted diseases. A device is provided which is placed in the cervical canal. Broadly, the device comprises an excipient and the agent. The invention, in its simplest and preferred embodiment comprises an excipient, the agent and an anchoring structure. In another embodiment of the invention, the excipient is used in combination with a housing, such as a biostable endo- or exoskeletal material, which housing is dimensionally stable. When used in combination with the housing, the excipient is bioerodible.

In another embodiment of the invention, the device is capable of the sustained release of such agents in the cervix over an extended period of time. This device can be composed of a hydrolytically unstable polymer matrix or a combination of a stable polymer and an erodible polymer that is capable of releasing the active agents over an extended period of time.

A polymeric excipient for the agent, and optionally a drug, can be any polymer or copolymer capable of providing slow and continuous release of this agent. An example is the group of copolymers synthesized from lactide and glycolide. A particularly preferred excipient is poly-D,L-lactic acid. Poly-L-lactic acid has been tested as a biodegradable carrier for the contraceptive steroid levenorgestrel at 33 w % loading in the matrix (J. M. Janckowicz, H. A. Nash, D. L. Wise, J. B. Gregory; Contraception, 8, 227; 1973). Copolymers of lactic and glycolic acids have also been tested in this context as excipients for injectable or implantable antimalarial drugs (D. L. Wise, G. J. McCormick, G. P. Willit, L. C. Anderson; Life Science, 19, 867; 1976) as well as for the naicetic antagonist naltrexone; A. D. Schwope, D. L. Wise, J. F. Howes, Life Sciences, 17, 1877; 1976).

The physical form of the active agents may vary. The metal. copper for example, may be present in ribbon, wire, powder form, or screen imbedded in the polymer. A drug, vibramycin ® for example, may be incorporated as the finely divided crystalline powder into the matrix or may be present as a solid solution therein or as the crystalline powder in equilibrium with its solution. The preferred active agent is an insoluble inorganic metal compound powder.

DESCRIPTION OF THE DRAWING(S)

FIG. 2 is a side view of one type of cervical device embodying the invention;

FIG. 3 is a bottom view of FIG. 2;

DESCRIPTION OF THE PREFERRED EMBODIMENT(S)

Agent Evaluation

Figure 1:
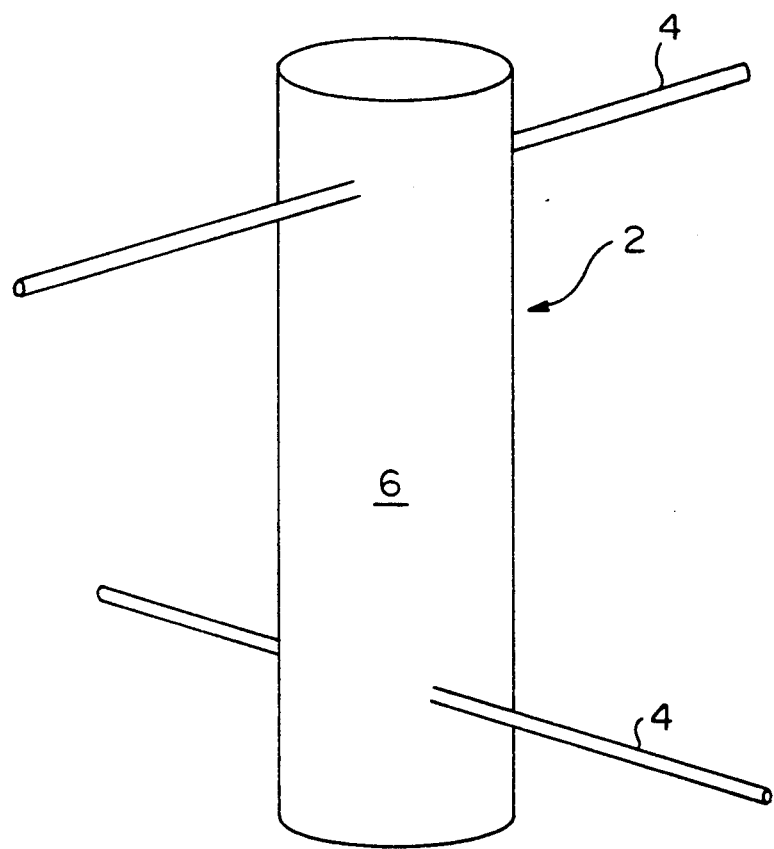
FIG. 1 is a side view of a cervical device embodying the invention.

For the evaluation of the efficacy of the spermicidal agents, the active agents selected for testing of efficacy as a spermicide where chosen based on certain criteria. The compounds chosen were metal salts, metal oxides or pure metal, all of which are insoluble and non-toxic. The original agents were tested in accordance with the F.D.A. protocol, volume 45, #241 of the Federal register. This protocol requires 1 gram of agent to be tested in 11 mL buffered saline and 0.2 mL sperm. The total test time allowed is 50 seconds. This test procedure was designed for soluble, vaginal contraceptive creams. The agents that passed under these constraints included: silver carbonate, silver (I) fluoride, silver lactate (slightly soluble), silver (I) peroxide, silver (II) oxide, silver phosphate and magnesium oxide. The following agents passed at a longer time than the allowed 50 second test time: zinc carbonate, cadmium oxide and arsenic.

Records were kept of the sperm concentration, motility, velocity, mean and max lateral head amplitude, beat cross frequency and solution pH. The total free metal ion concentration was calculated in order to confirm that agent activity is not a function of free ion concentration. A pH sperm survival curve was constructed which showed that sperm are unaffected between pH 3.1 and 11.7.

Because the device dimensions prohibit an active agent release rate of 1 gram/day, lower concentrations, 100 mG and 10 mG of each agent were tested at pH 7.0. All agents which passed the original test, also passed under physiological pH. The agents that passed at 100 mG per 11 cc of solution included the following: silver fluoride, silver (I) oxide, silver (II) oxide and silver phosphate (poor motility). Agents that passed at 10 mG per 11 cc of solution included the following: silver (II) oxide and silver fluoride (poor motility).

All of the agents that passed the F.D.A. protocol were then subjected to sperm migration tests in bovine cervical mucus. The testing protocol used was similar to that done by J. Botella-Llusia and V. Riuz-Velasco ("Postcoital Test In Vitro", Inter. J. Fert., therefore 5 therefore 301 1960). 0.2 mL of sperm were placed in an 8 mM id test tube in a constant temperature bath. Bovine cervical mucus and 10 mG of the agent to be tested were mixed and drawn up into the full tip of a transfer pipette. The pipette was then placed into the test tube. After 90 minutes, the pipette was sliced at 20 mM intervals and the contents of each section were studied for sperm presence and motility.

The results from this testing method showed that a number of agents were effective in preventing sperm motility. The best compounds were: silver fluoride, silver (II) oxide, silver carbonate, silver phosphate and magnesium peroxide. Although these compounds still allowed sperm migration up to the 60 mM section, in all cases, there were no motile sperm in either the sperm reservoir (test tube) or in any of the sections of the pipette, except in the case of the control. The control, which consisted of the sperm and pure bovine cervical mucus, showed motile sperm up to 120 mM and in the reservoir.

Test Procedures

For the invention disclosed herein, testing techniques were created which took into account not only the placement of the device in the cervical canal, but also the fact that the agents are insoluble. There are no literature references which discuss testing techniques appropriate for such a device. There is a need for both increased test time and decreased concentration of agent. It is believed that an increase in the testing time is acceptable since studies indicate that sperm normally migrate an average of 2–3 mM per minute (Davajan, V., Nakamura, R., and Kharma, K., "Spermatozoon Transport in Cervical Mucus", Obstetrical and Gynecological Survey, 1969).

The use of animals, and specifically rabbits, for contraceptive testing is well established, as seen by the articles mentioned previously by Zipper and Chang ("The Effect of Contraceptive Jellies Placed into the Rabbit Vagina Before Mating", Fer. and Steril., 11, 1, 1960) which discusses that rabbits are a good model because rabbit sperm are more resistant to spermicidal agents than human sperm; therefore efficacy in rabbits very strongly suggests efficacy in humans. The support for rabbit models is also found in the review by Millman, and a Mimeograph by the Planned Parenthood Federation of America written by C. Hartman in 1958.

An animal study was conducted using the active agent, silver (II) oxide, in a controlled release device in the rabbit to demonstrate the efficacy of this approach.

EXAMPLE

Referring to FIG. 1, intracervical devices 2 were prepared by compounding Ag (II)0 powder (99.9+%  pure) with poly-(d,1-lactic) acid. The active agent was 30% by weight of the total weight of the device (less the prongs). The compound was extruded and cut into rods 4 millimeters in diameter and 20 millimeters in length. Two polypropylene prongs 4 were inserted at right angles to one another about $\frac{1}{3}$ the distance from each end of a rod 6, see FIG. 1. The prongs, 0.1 mm in diameter, extended approximately 10 millimeters from the surface of the rod 6. The device 2 of FIG. 1 embodies the preferred embodiment and an embodiment of the invention in a basic form.

Fourteen New Zealand white rabbits bred at Millbrook Farms, Amherst, Mass., were used. Four rabbits were used as controls. Ten rabbits had the devices implanted surgically in both cervices. The duration of the tests ranged from two to six weeks.

At the time of necropsy, all four control rabbits were pregnant. Six of the ten test rabbits that had the devices implanted also became pregnant. However, none of these six had the devices in place at the time of the necropsy. It was postulated that the device was expelled prior to conception. The devices were not sutured in place but relied upon the prongs for support in the rabbits' cervix. These devices were designed for the human cervix and appear to be unsatisfactory in the rabbit.

More importantly, the remaining four test rabbits did not become pregnant and at the time of necropsy, had at least one device still implanted in the cervix. Because these rabbits remained non-gravid, it was concluded that as long as one device was present there was protection because all controls became pregnant. The device used did not include a dimensionally stable housing. The rod was completely erodible.

THE DEVICE

These studies support the hypothesis that the device prevents conception. Device expulsion was the cause for the 60% of the rabbits that become pregnant. Further, the Botella-Llusia modification for testing the efficacy of such insoluble agents supports the observed results.

In the preferred embodiment of the invention, an insoluble metallic salt or combination of salts with the metal selected from the groups consisting of silver, magnesium, zinc or copper is used. In a particularly preferred embodiment, the salts are selected from the group consisting of silver carbonate, silver (I) fluoride, silver (I) oxide, silver (II) oxide, silver phosphate and magnesium peroxide. Slightly soluble inorganic metal salts such as silver lactate have also been shown to be efficacious, however, the goal of the invention is to have nonabsorbable and/or insoluble agents that cannot become systemic in their action. Thus, the preferred embodiment of this invention employs insoluble agents.

The delivery device consists either entirely of, or partially of, an erodible polymer capable of a continuous and sustained release of these insoluble agents over periods of time ranging up to eighteen months. Polymers of lactic and glycolic acid have been evaluated for this purpose and have demonstrated controlled release times up to one year. Other polymers, such as the polyanhydrides and other polyesters, may also be used to deliver these insoluble agents.

Another nonerodible polymer can be mixed with the degrading polymer in such a manner that both polymer phases are continuous. These bicontinuous or co-continuous matrices are also useful for the delivery of the insoluble agent(s). An important feature of these polyblends is the generation of the proper phase heterogeneity to allow for the continuous release of the insoluble agent. The phase heterogeneity also dictates the rate in which the erodible polymer degrades, thus acting as a control release mechanism in these systems. Further, such polymers may act as mechanical supports or as a nonerodable skeletal structure of the device Nonerodible polymers comprise ethylene-vinyl acetates where the content of the vinyl acetate can range from 10 to 40%. Other polymers, such as polyamides, polyalkyls, polyesters, polyethers, etc. may also be employed as long as they do not homogeneously mix with the degradable polymer.

The proportion of the erodible to nonerodible polymer components may vary from 30 to 70% of each respective component in the other component. Thus, polyblends have been prepared that show bicontinuity in both phases from poly(d,1-lactic acid) (PLA) and ethylene-vinyl acetate copolymer (EVAc) from 30% PLA to 70% PLA in EVAc, all of which show continuity in both phases. This system shows the widest variation of composition with the maintenance of the bicontinuous character of both phases. As stated previously, because the release mechanism is based upon the erosion of the hydrolytically unstable polymeric phase, this phase must be continuous and exposed to the environment to allow for the release of the insoluble agent. Other polyblends generally show a much narrower window of acceptable mix ratios to allow for the generation of the bicontinuous phases. Many polyblends do not form co-continuous or bicontinuous phases at any composition and therefore would be unsuitable for this device and application.

Blending techniques that may be employed for the generation of these bicontinuous matrices include mechanical and solution blending. Mechanical blending, e.g. extrusion, milling, etc., results in heterogeneous phases that vary according to the time and extent of mixing performed by the technique. In general, mechanical mixing techniques result in large phases as compared to solution blending techniques. The large phase heterogeneity that results from most types of mechanical mixing produces polyblends that show shorter degradation times for the erodible phase. Thus, samples prepared using techniques such as single screw extrusion or melt extrusion show device lifetimes up to twelve months in duration.

Solution blending allows for the generation of a considerably finer structure in the phases. Electron microscopy reveals that in solution blending of PLA with EVAc average pore structures on the order of 15-20 microns are formed. These types of blends allow for the continuous and sustained release of an insoluble active agent up to 12 to 18 months. Polymer erosion, and hence the rate of release, are controlled by the dimensions of the heterogeneous phases, although the small structures generated by solution blending may not allow for the complete delivery of the insoluble agent. The insoluble agent can become trapped within the small pores of the bicontinuous blends and is therefore unavailable for the intended application. Release amounts will vary from 30% of the original weight of the insoluble agent to as high as 90% in blended systems. An important feature of this system is to balance the duration of controlled release with the amount of material to be released.

The active agent(s) may be blended in at the time of the preparation of the device or may be blended into only one of the phases prior to mechanical blending. When the insoluble agent(s) are blended in at the time of the fabrication of the device, some of the active agent becomes trapped into the nonerodible portion of the system when a polyblend device is prepared. Solution blending always results in the uniform dispersion of the active agent(s) throughout both phases. Dispersal of the active agent into the erodible portion either through solution blending or mechanical mixing, confines the active agent to this phase only and therefore makes to more available for release from the total device.

The agents can be incorporated into the excipient in the form of powders and in amounts of 1-70%, preferably 30-50%, by weight based on the weight of the erodible excipient.

Drugs, soluble or insoluble, that can be delivered include antibiotics, such as tetracycline; anti-bacterials such as sulfonamides; anti-inflamatories, such as dexamathsone; hormonal agents, such as prostaglandin $F_2$; antiviral agents, such as CPF; and the like. These drugs are added in amounts of 0.001 to 10.0% by weight based on the total weight of the excipient (not including the weight of the agent or drug).

Referring to FIGS. 2 and 3, a device embodying the invention is shown generally at 10 for insertion within the canal of the cervix of the uterus. The device 10 comprises a vertical stem portion 12 comprising a poly(d,1-lactic acid)/silver oxide matrix coated with a silicon rubber 14. The coating has embedded therein a string 16 allowing for device removal. Extending outwardly from the stem portion are prongs 20, such as polypropylene or nylon fibers. Typically the device is 20 millimeters long and 4 millimeters in diameter. The prongs are about 20 millimeters. The prongs serve to anchor the device in place so that it will not be expelled from the internal OS of the cervix. The matrix has a specific composition of poly(d,1-lactic acid) blended with 30% by weight of insoluble active agent.

Figure 4:
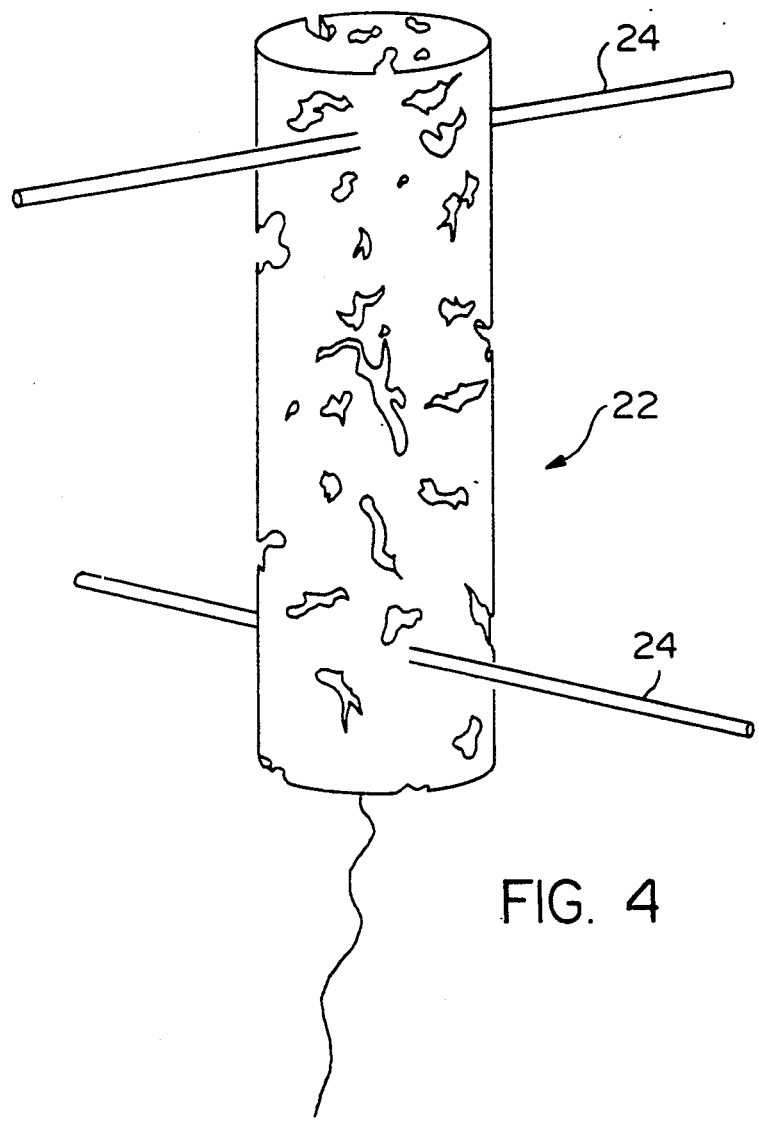
FIG. 4 is an alternative embodiment of the invention.

FIG. 4 shows an intracervical device 22 comprising a combination of 30-70% ethylene vinyl acetate and 70-30% by weight poly(d,1-lactic) acid with extending arms 24, and with 30-50% by weight agent based on the weight of the poly(d,1-lactic) acid (excipient) in the composition.

Figure 5:
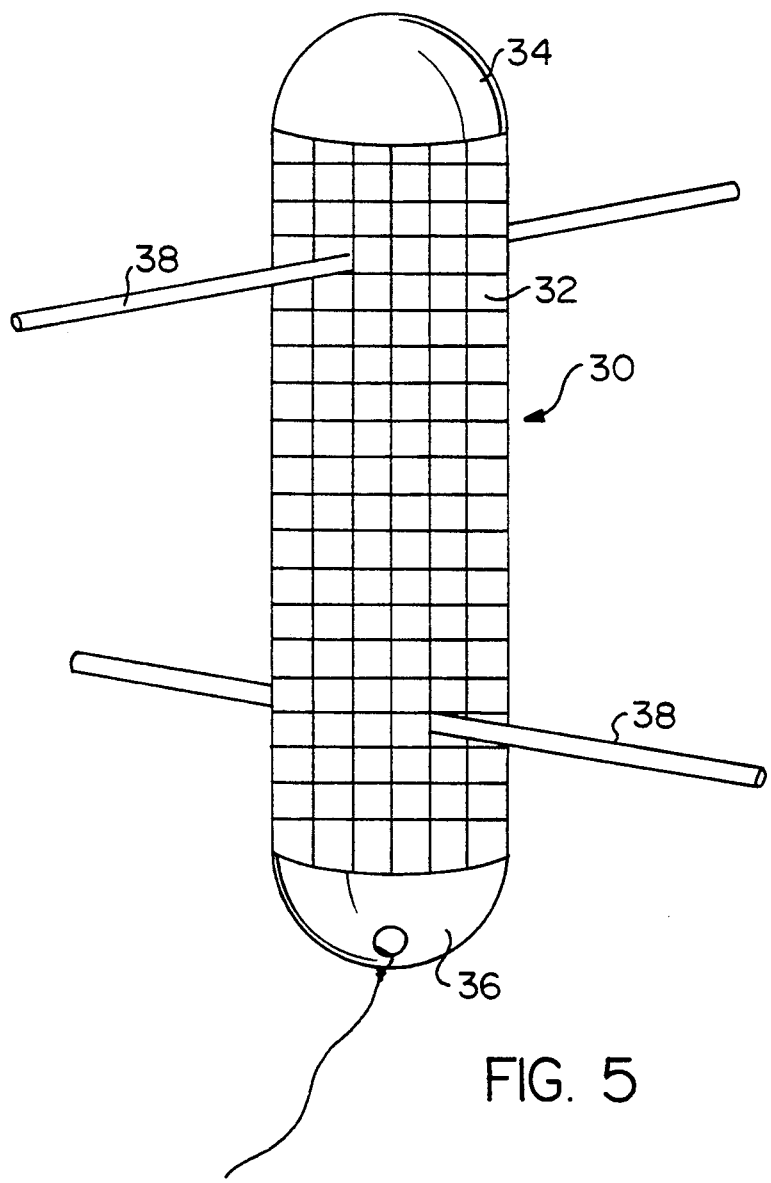
FIG. 5 is a further alternative embodiment of the invention.

FIG. 5 is a further alternative invention of an intracervical device 30, wherein the delivery medium is received within a polyethylene or polypropylene mesh 32 and includes a cap 34 to seal one end of the mesh and a polyethylene or polypropylene eyelet 36 for string attachment at the other end. It further includes nylon or polyethylene or polypropylene arms 38.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. An intracervical device which comprises:
   a spermicidal composition which consists of an effective amount of an agent selected from the group consisting of silver, magnesium, zinc, copper, cadmium or arsenic and their salts and oxides for use as a contraceptive device;
   the agent being imbedded an excipient, the excipient comprising an erodible polymer which controls the release rate of the agent;
   means to secure the device in the cervix; and
   means to remove the device from the cervix.

2. The device of claim 1 wherein a metal selected fron the group consisting of silver, magnesium, zinc, copper, cadmium or arsenic is combined with a complementary anion selected from the group consisting of carbonates, phosphates, halides, lactates, oxides or peroxides to form insoluble metal salts or metal oxides.

3. The device of claim 1 wherein the agent is present in an amount of 30-50% by weight based on the weight of the excipient.

4. The device of claim 1 wherein the erodible polymer is selected from the group consisting of lactic and glycolic acids and polyanhydrides and polyesters.

5. The device of claim 1 which comprises a biostable skeletal polymer mixed with the excipient.

6. The device of claim 5 wherein the biostable polymers are selected from the group consisting of ethylene vinyl acetates, polyamides, polyalkyls, polyesters and polyethers.

7. The device of claim 5 wherein the proportion of the erodible polymer to the skeletal polymer varies from 30 to 70% in each of the respective phases.

8. The device of claim 2 wherein the agent is a silver or magnesium salt.

9. The device of claim 1 which includes:
   a drug selected from the group consisting of antivirals, antibiotics, antibacterials, anti-inflammatories, or hormonal agents.

10. The device of claim 1 wherein the means to anchor the device within the cervix comprises prongs extending from the device.

11. The device of claim 1 wherein the means to secure the device in the cervix comprises a housing within which is secured the device.

12. The device of claim 11 wherein the housing comprises a polymeric support structure having prongs extending outwardly therefrom.

13. The device of claim 1 wherein the means to remove the device comprises a string.

14. A spermicidal composition which consists of:

an effective amount of an agent selected from the group consisting of silver, magnesium, zinc, copper, cadmium or arsenic and their salts and oxides for use as a contraceptive device; and an excipient, the excipient comprising an erodible polymer which controls the release rate of the agent; said agent being imbedded in said excipient.

15. The composition of claim 14 therefor wherein a metal selected from the group consisting of silver, magnesium, zinc, copper, cadmium or arsenic is combined with a complementary anion selected from the group consisting of carbonates, phosphates, halides, lactates, oxides or peroxides to form insoluble metal salts or metal oxides.

16. The composition of claim 1 therefor wherein the erodible polymer is selected from the group consisting of lactic and glycolic acids and polyanhydrides and polyesters.

17. The composition of claim 14 therefor which includes:

a drug selected from the group consisting of antivirals, antibiotics, antibacterials, anti-inflammatories, or hormonal agents.

* * * * *